United States Patent [19]

Andresen et al.

[11] 4,274,841
[45] Jun. 23, 1981

[54] ACETYLENE RECOVERY PROCESS AND APPARATUS

[75] Inventors: Harvey E. Andresen; Thomas F. Persohn, both of Charleston, W. Va.

[73] Assignee: Union Carbide Corporation, New York, N.Y.

[21] Appl. No.: 134,948

[22] Filed: Mar. 28, 1980

[51] Int. Cl.³ .............................................. B01D 53/16
[52] U.S. Cl. .......................................... 55/40; 55/48; 55/49; 55/51; 55/64; 55/195; 202/177; 203/27
[58] Field of Search .............................. 55/40, 48–51, 55/63–65, 195; 202/177, 180; 203/21, 22, 27

[56] References Cited

U.S. PATENT DOCUMENTS

| 1,900,655 | 3/1933 | Metzger | 55/51 X |
|---|---|---|---|
| 2,146,448 | 2/1939 | Scott et al. | 55/65 X |
| 2,742,102 | 4/1956 | Eichmann | 55/40 X |
| 2,891,633 | 6/1959 | Morro, Jr. et al. | 55/65 X |
| 3,034,272 | 5/1962 | Griffin et al. | 55/65 |
| 4,184,855 | 1/1980 | Butwell et al. | 55/49 X |

FOREIGN PATENT DOCUMENTS

| 621103 | 5/1961 | Canada | 55/51 |
|---|---|---|---|
| 37-956 | 4/1962 | Japan | 55/65 |

Primary Examiner—Robert H. Spitzer
Attorney, Agent, or Firm—Gerald R. O'Brien, Jr.

[57] ABSTRACT

Improved process and apparatus is disclosed for the recovery of acetylene from gas containing acetylene and ethylene comprising: contacting said gas with acetylene solvent to form a loaded solvent solution; heating said loaded solvent solution by passing through a first stream conduit of a heat exchange zone having a plurality of non-interconnecting stream conduits in heat exchange thermal contact; separating the resulting liquid/vapor into liquid and vapor phases; passing said liquid phase to a second stream conduit of said heat exchange zone passage to a downstream further acetylene separation purification step; and cooling warm denuded acetylene solvent by passage through a third stream conduit of said heat exchange zone and then further cooling before passage to said acetylene solvent contacting zone.

8 Claims, 4 Drawing Figures

ACETYLENE RECOVERY PROCESS AND APPARATUS

The present invention relates to improved acetylene recovery process and apparatus therefor and, more particularly, to use in connection with the interstage processing of acetylene-containing gas in a three-column acetylene separation recovery unit.

Heretofore, many types of three-column acetylene recovery unit systems have been proposed, such as that specifically shown in U.S. Pat. No. 2,891,633. As shown in FIG. 1 of that patent, the three-column acetylene recovery unit comprises an acetylene absorber column, a vent column and an acetylene still column. In practice, such units have been designed to require the consumption of relatively large quantities of utility steam, refrigerant and cooling water. Such units require the consumption of considerable external energy and result in a considerable increase in over-all operating cost of the system.

It is the prime objective of the present invention to provide process and apparatus for such acetylene recovery in which the consumption of external energy streams is significantly reduced and wherein the energy within the system is more efficiently utilized. Another objective is to reduce the initial complexity of the overall system and the consequent initial investment thereof.

In accordance with one aspect of the present invention, an improved process is provided for the recovery of acetylene from a feed gas stream containing acetylene and ethylene and produced by the cracking of hydrocarbon feedstock. Such process comprises the steps of: contacting said gas stream in a contacting zone under pressure with an acetylene solvent in a quantity sufficient for the absorption of substantially all of the acetylene and some of the ethylene of said feed gas stream to form a loaded solvent solution; warming and partially boiling said loaded solvent solution by passing through a first stream conduit of a zone having a plurality of non-interconnecting stream conduits passing therethrough in heat exchange thermal contact; separating the resulting liquid/vapor mixture and recycling said vapor phase to the liquid discharge region of said contacting zone; passing the liquid phase to a second stream conduit of said zone having a plurality of non-interconnecting stream conduits passing therethrough in heat exchange thermal contact, thereby permitting the temperature thereof to drop substantially before said liquid phase passes on to a downstream further separation step for the removal of further purified acetylene product; and warm denuded acetylene solvent is cooled to lower temperature initially by passage through a third stream conduit of said zone having a plurality of non-interconnecting stream conduits passing therethrough in heat exchange thermal contact and then further cooling before passage to said acetylene solvent contacting zone; whereby greater thermal efficiency is effected in the process.

Figure 1:
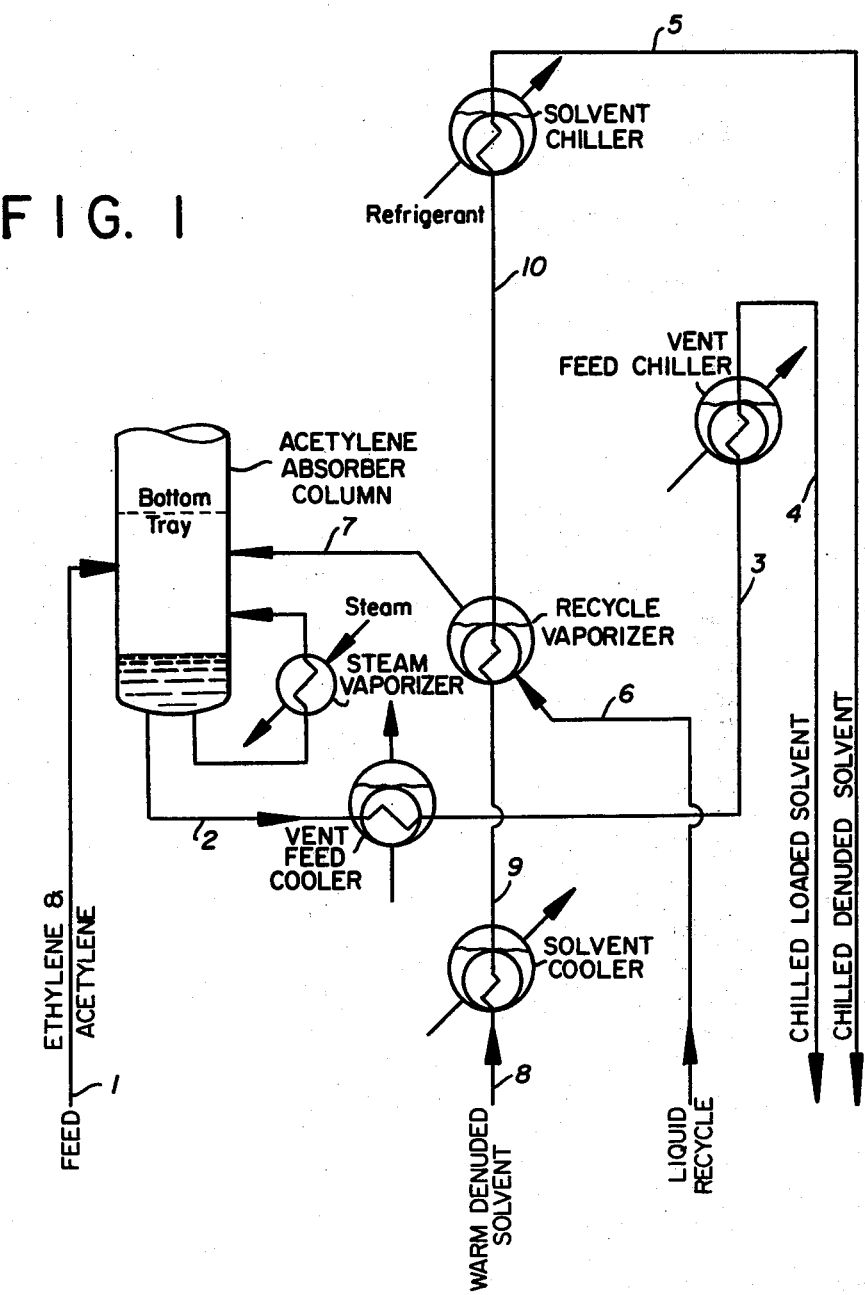
FIG. 1 is a simplified schematic flow diagram of conventional apparatus suitable for the practice of prior interstage process (between the acetylene absorber column and the vent column)

The conventional or prior art process employs apparatus as shown in FIG. 1 of the drawings. As there shown, the ethylene and acetylene gas mixture is fed to the lower portion of an acetylene absorber column at a point below the bottom tray and above the liquid level in the column. The process of the invention is not limited to the use of any particular acetylene solvent and any solvent which is capable of dissolving acetylene more selectively than ethylene and other constituent gases may be employed. Such solvents comprise, for example, methanol, dimethylformamide, methyl ethyl ketone, butyro lactone and acetone. Dimethylformamide has been found to be a preferred solvent.

Liquid, in the form of loaded solvent, is passed from the bottom of the acetylene absorber column through two independent vent feed coolers before passage to the downstream vent column. Warm denuded solvent is similarly passed through two independent coolers before passage from the interstage system. Liquid recycle is passed through a recycle vaporizer before introduction into the bottom of the acetylene absorber column. A portion of the liquid from the bottom of the acetylene absorber column is also steam vaporized and reintroduced into the area between the bottom tray and the liquid surface within the acetylene absorber column.

Figure 2:
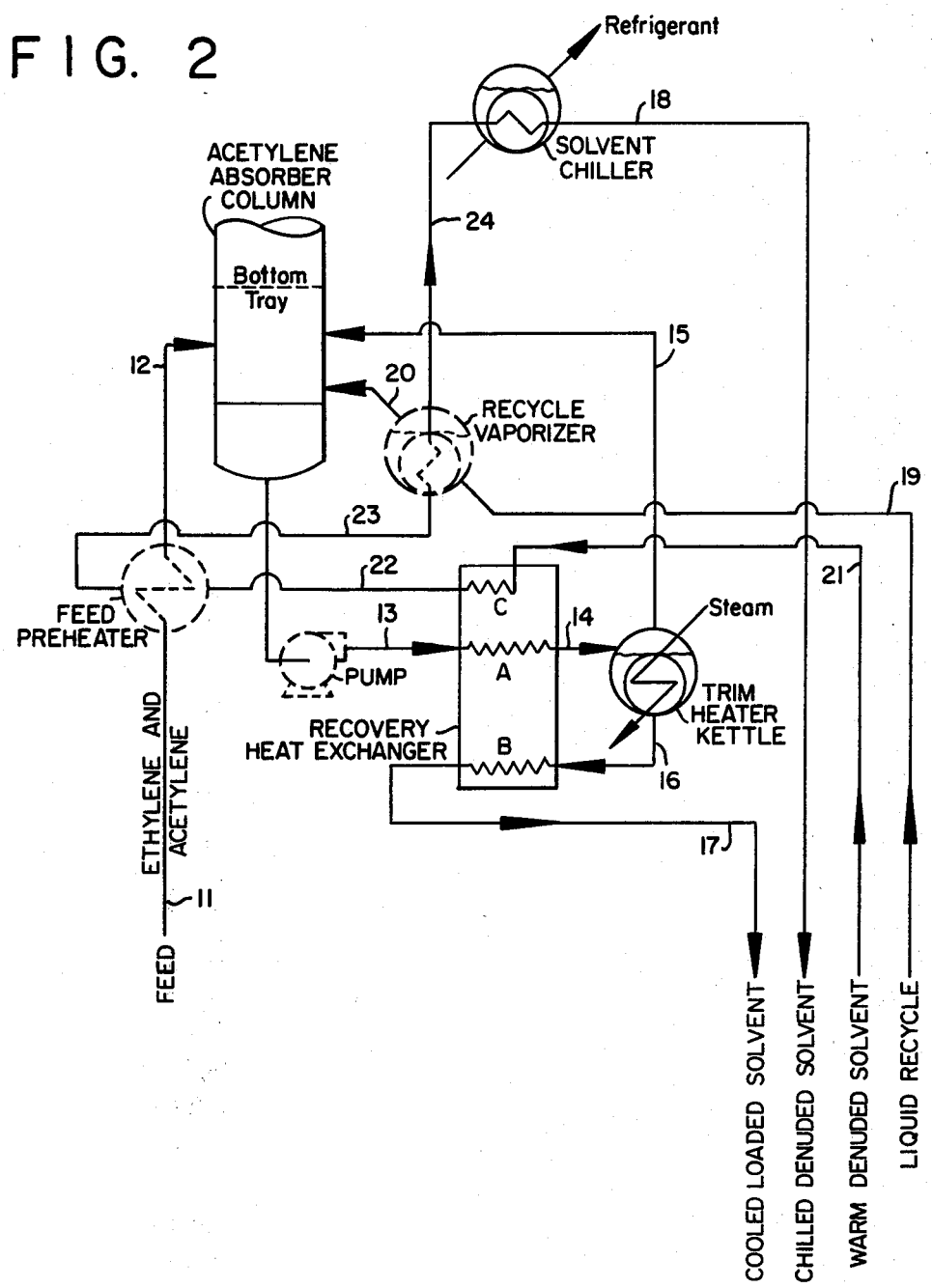
FIG. 2 is a simplified schematic flow diagram of apparatus suitable for carrying out the improved process of the present invention.

The preferable apparatus for practicing the process of the present invention is shown in FIG. 2 of the drawings. In comparison to the conventional apparatus of FIG. 1, an optional inlet gas feed preheater is provided prior to the introduction of feed into the bottom of the acetylene absorber column as shown in FIG. 2. The feed enters the absorber at 300 psia as vapor at 9° C. at the rate of about 123,000 pounds per hour. The objective of the optional feed preheater is to recover refrigerant. The composition of the pre-heated feed is 0.9886 mole fraction ethylene and 0.0114 mole fraction acetylene. In the column, all of the acetylene and some of the ethylene is absorbed in the acetone solvent. The liquid flows to the bottom of the absorber column and exits through an optional pump at a flow rate of 148,000 pounds per hour, temperature of approximately −8° C. and a composition of 0.0358 mole fraction acetylene, 0.3132 mole fraction ethylene and 0.6505 acetone mole fraction. This mixture is warmed and partially boiled in the recovery heat exchanger passage A and flows as a liquid/vapor mix to the trim heater kettle. Here the vapor flows overhead and the liquid is further heated to 90° C. using steam as a heating medium. The additional vapor generated in the trim heater flows with the flashed vapor phase to the base of the absorber column. The liquid composition is now 0.0249 acetylene, 0.0854 ethylene and 0.8901 acetone and the flow rate is 119,000 pounds per hour. This liquid flows to passage B of the recovery heat exchanger where it is cooled, thereby providing heat for exchange to passage A. The flow rates and compositions do not change, but the temperature drops to 30° C. This temperature is governed by the critical design of the heat exchanger as is well known to those skilled in this design art. The liquid flows to the ethylene vent column for further processing.

The warm denuded solvent is chilled to −33° C. in four stages: the first stage is passage C of the recovery heat exchanger, the pure acetone solvent at 78° C. flowing at 118,000 pounds per hour is cooled to +5.3° C. (the sensible heat being transferred to passage A); the solvent being further cooled to −14.5° C. in the optional feed preheater and then to −24.6° C. in the optional recycle vaporizer; and finally cooled to −33° C. using the refrigerant action of the solvent chiller.

A brazed aluminum plate and fin type heat exchanger is preferably employed as the recovery heat exchanger. Such a heat exchanger employs aligned plate blocks having internal set of fluid channels, the plate blocks being successively brazed to each other to provide the required thermal contact. Such a heat exchanger provides for the development of a thermal gradient across its transverse section, i.e., the section shown schematically in FIG. 2 of the drawings. Other suitable equivalent types of heat exchangers may, however, be operably employed as the recovery heat exchanger in the apparatus aspect of the present invention.

It is to be noted that the vent feed cooler and the vent feed chiller of the conventional system of FIG. 1 have been eliminated. As a result of the warmer absorber temperature of the process of the invention as shown in FIG. 2, the need for the conventional process' cold (−27° C.) vent column feed is eliminated. Also, the vent column reboiler heat requirement (and consequently column diameter) is decreased. Passage C of the recovery heat exchanger contains warm denuded solvent. This passage, like passage B, flows countercurrent to passage A. The denuded solvent exits the recovery heat exchanger at −3° C. where it is then cooled against recycle ethylene and subsequently against propylene refrigerant, thereby eliminating the use of external utility solvent cooler (30–50 psi propylene refrigerant).

It is further to be noted that the recovery heat exchanger must be properly designed to take maximum benefit of the available heat. The design of the recovery heat exchanger must be nearly true counterflow in order to achieve the optimal operability.

The recovery heat exchanger, shown in the process flow diagram of FIG. 2 and described herein as a plate and fin heat exchanger, is designed for a 5° C. temperature approach on the cold end. Relative equipment/energy costs at the time of the design will dictate the approach temperature and hence exchanger size used.

A booster pump is shown on the column kettle liquid. Its purpose is to overcome pressure drop in the recovery heat exchanger. The pump can be eliminated if the column is elevated or a high liquid level is maintained in the column base. This results in a larger recovery heat exchanger as the required lower pressure drop results in a lower over-all heat transfer coefficient. Relative equipment costs will dictate whether or not the booster pump is used.

Figure 3:
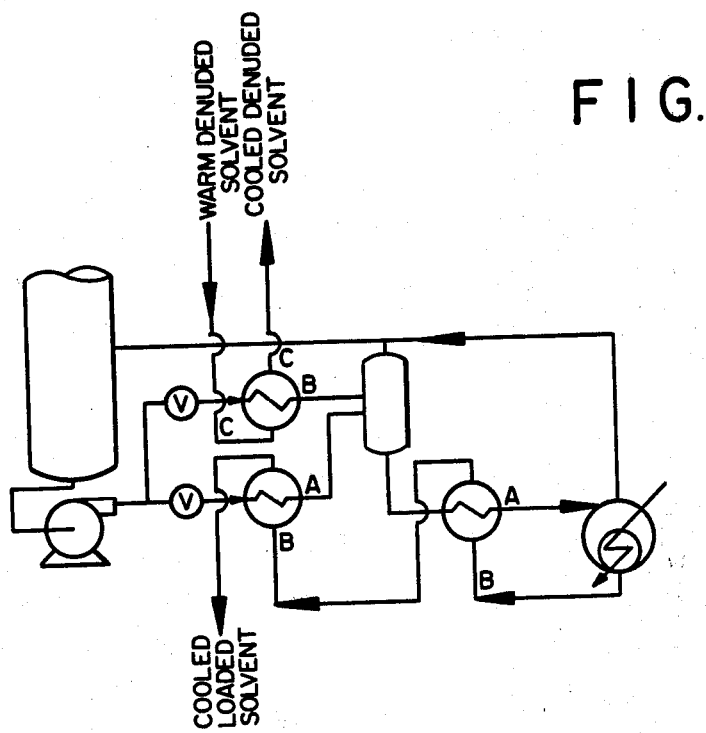
FIG. 3 is a simplified schematic representation of apparatus equivalent to that of FIG. 2 employing conventional counterflow shell and tube heat exchangers in place of the single plate and fin recovery heat exchanger of FIG. 2.

Conventional counterflow shell and tube heat exchangers can be substituted for the plate and fin units shown. Multiple shell and tube exchangers are needed to match performance of this single plate and fin unit. FIG. 3 of the drawings shows such an arrangement.

As indicated hereinabove, any other counterflow heat exchanger can be substituted. The temperatures and pressures shown can be optimized with respect to other portions of the plant.

The process can be made to function satisfactorily without the trim heater kettle. In this process, the solvent water cooler (cools solvent from 80° to 45° C.) is bypassed or eliminated. The hot solvent is now the only heat source for the acetylene absorber kettle. Very little additional utility or refrigerant consumption results from elimination of the trim heater. However, the system is judged to be more difficult to operate as one degree of freedom is lost.

Figure 4:
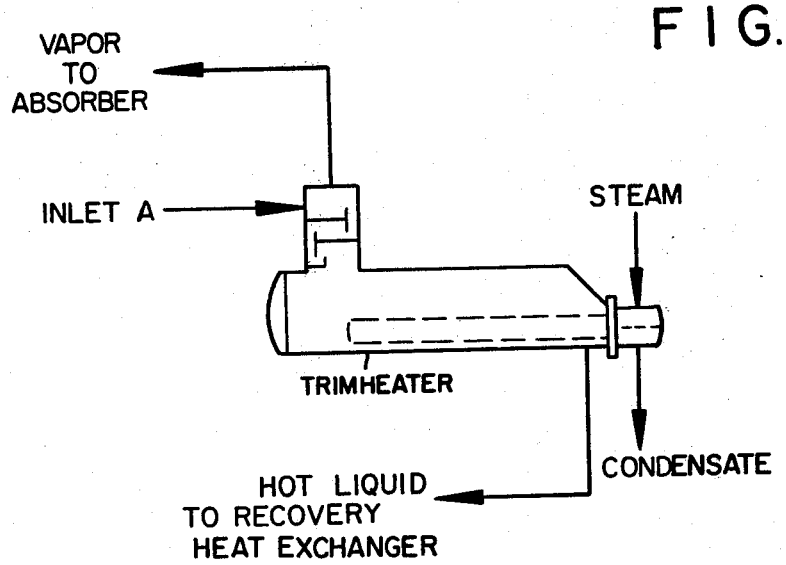
FIG. 4 is a simplified schematic representation of an improved optional tray section incorporated above the steam heater otherwise shown in FIG. 2 of the drawings.

A small reduction in refrigeration requirement can be obtained by installing a tray section above the trim heater as shown on FIG. 4. This removes an increment of heat from the trim heater vapor which would otherwise uselessly heat the absorber column.

The following TABLES I and II set forth respectively data for the operation of a conventional system of prior art (as set forth schematically in FIG. 1 of the drawings) and for the system of the present invention (as schematically shown in FIG. 2 of the drawings). The data sets forth the various parameters including stream state, flow temperature and composition values for different streams in the conventional system and the system of the present invention. It is to be noted that such stream data is set forth for ten (10) locations in the conventional system (TABLE I) and fourteen (14) locations in the system of the present invention (TABLE II).

TABLE I

| Stream | 1 | 2 | 3 | 4 | 5 | 6 | 7 | 8 | 9 | 10 |
|---|---|---|---|---|---|---|---|---|---|---|
| State (liquid or vapor) | V | L | L | L | L | L | V | L | L | L |
| Flow (M lb/hr) | 123 | 150 | 150 | 150 | 144 | 14 | 14 | 144 | 144 | 144 |
| Temperature (°C.) | −24 | +50 | −7 | −27 | −27 | −69 | −24 | +43 | 0 | −21 |
| Composition (mole fractions): | | | | | | | | | | |
| Acetylene | .0157 | .0276 | .0276 | .0276 | Trace | .0204 | .0204 | Trace | Trace | Trace |
| Ethylene | .9843 | .1716 | .1716 | .1716 | 0 | .9765 | .9765 | 0 | 0 | 0 |
| Acetone | 0 | .8008 | .8008 | .8008 | 1.0 | .0031 | .0031 | 1.0 | 1.0 | 1.0 |
| TOTAL | 1.0 | 1.0 | | | | | | | | |

TABLE II

| Stream | 11 | 12 | 13 | 14 | 15 | 16 | 17 | 18 | 19 | 20 | 21 | 22 | 23 | 24 |
|---|---|---|---|---|---|---|---|---|---|---|---|---|---|---|
| State (liquid or vapor) | V | V | L | L & V | V | L | L | L | L | V | L | L | L | L |
| Flow (M lb/hr) | 123 | 123 | 148 | 148 | 29 | 119 | 119 | 118 | 5.3 | 5.3 | 118 | 118 | 118 | 118 |
| Temperature (°C.) | −24 | −9 | +0.3 | +79 | +80 | +95 | +30 | −33 | −66 | −29 | +78 | +5.3 | −14.8 | −25.6 |
| Composition (mole fractions): | | | | | | | | | | | | | | |
| Acetylene | .0114 | .0114 | .0358 | .0358 | .0621 | .0244 | .0244 | Trace | .0200 | .0200 | Trace | Trace | Trace | Trace |
| Ethylene | .9886 | .9886 | .3132 | .3132 | .8401 | .0854 | .0854 | 0 | .9800 | .9800 | 0 | 0 | 0 | 0 |

TABLE II-continued

| Stream | 11 | 12 | 13 | 14 | 15 | 16 | 17 | 18 | 19 | 20 | 21 | 22 | 23 | 24 |
|---|---|---|---|---|---|---|---|---|---|---|---|---|---|---|
| Acetone | 0 | 0 | .6505 | .6505 | .0966 | .8901 | .8901 | 1.0 | 0 | 0 | 1.0 | 1.0 | 1.0 | 1.0 |

It is to be noted by a comparison of the flow sheets of FIGS. 1 and 2 that much of the externally supplied utilities of the conventional system have been eliminated in the system of the present invention. In addition, a reduction in the number of secondary vessels has been effected, the duties of many of the prior art (conventional) vessels being carried out in the recovery heat exchanger of the system of the present invention. Accordingly, considerable savings in utilities (e.g., steam and refrigeration) are achieved while still effecting the desired results. There is, in addition, a reduction in apparatus capital investment in reducing the number of vessels employed in the system. Further, there is some heat efficiency employment in centralization of steps in the recovery heat exchanger which were carried out in isolated vessels in the prior art (conventional) system.

What is claimed is:

1. An improved process for the recovery of acetylene from gas containing acetylene and ethylene comprising: contacting said gas with an acetylene solvent to form a loaded solvent solution; warming and partially boiling said loaded solvent solution by passing through a first stream conduit of a heat exchange zone having a plurality of non-interconnecting stream conduits passing therethrough in heat exchange thermal contact; separating the resulting liquid/vapor mixture and passing the liquid phase to a second stream conduit of said heat exchange zone, thereby permitting the temperature thereof to drop substantially before said liquid phase passes on to a downstream further separation step for the removal of further purified acetylene product; and warm denuded acetylene solvent is cooled to lower temperature initially by passage through a third stream conduit of said heat exchange zone and then further cooling before passage to said acetylene solvent contacting zone; whereby greater thermal efficiency is effected in the process.

2. The process of claim 1, wherein said solvent is selected from the group consisting of methanol, dimethylformamide, methyl ethyl ketone, butyro lactone and acetone.

3. In an improved process for the recovery of acetylene from a feed gas stream containing acetylene and ethylene and produced by the cracking of hydrocarbon feedstock, which process comprises the steps of: contacting said gas stream in a contacting zone under pressure with an acetylene solvent in a quantity sufficient for the absorption of substantially all of the acetylene and some of the ethylene of said feed gas stream to form a loaded solvent solution; warming and partially boiling said loaded solvent solution by passing through a first stream conduit of a heat exchange zone having a plurality of non-interconnecting stream conduits passing therethrough in heat exchange thermal contact; passing the resulting liquid/vapor mixture of a heating zone wherein the vapor phase bypasses said heating zone and the liquid phase is further heated employing a heating medium external to the system to produce additional vapor which is recycled with said vapor phase to the liquid discharge region of said contacting zone; said liquid phase being passed to a second stream conduit of said heat exchange zone having a plurality of non-interconnecting stream conduits passing therethrough in heat exchange thermal contact, thereby permitting the temperature thereof to drop substantially before said liquid phase passes on to a downstream further separation step for the removal of further purified acetylene product; and warm denuded acetylene solvent is cooled to lower temperature initially by passage through a third stream conduit of said heat exchange zone having a plurality of non-interconnecting stream conduits passing therethrough in heat exchange thermal contact, and then further cooling before passage to said acetylene solvent contacting zone; whereby greater thermal efficiency is effected in the process.

4. The process of claim 3, wherein said solvent is selected from the group consisting of methanol, dimethylformamide, methyl ethyl ketone, butyro lactone and acetone.

5. In an improved process for the recovery of acetylene from a feed gas stream containing acetylene and ethylene and produced by the cracking of hydrocarbon feedstock, which process comprises the concurrent steps of: contacting said gas stream in a contacting zone under pressure with an acetylene solvent in a quantity sufficient for the absorption of substantially all of the acetylene and some of the ethylene of said feed gas stream to form a loaded solvent solution; warming and partially boiling said loaded solvent solution by passing through a first stream conduit of a heat exchange zone having a plurality of non-interconnecting stream conduits passing therethrough in heat exchange thermal contact; passing the resulting liquid/vapor mixture to a heating zone wherein the vapor phase bypasses said heating zone and the liquid phase is further heated employing a heating medium external to the system to produce additional vapor which is recycled with said vapor phase to the liquid discharge region of said contacting zone; said liquid phase being passed to a second stream conduit of said heat exchange zone having a plurality of non-interconnecting stream conduits passing therethrough in heat exchange thermal contact, thereby permitting the temperature thereof to drop substantially before said liquid phase passes on to a downstream further separation step for the removal of further purified acetylene product; and warm denuded acetylene solvent is cooled to lower temperature initially by passage through a third stream conduit of said heat exchange zone having a plurality of non-interconnecting stream conduits passing therethrough in heat exchange thermal contact, and then, by further cooling in at least one subsequent conventional cooler zone, before passage to said acetylene solvent contacting zone; whereby greater thermal efficiency is effected in the process.

6. The process of claim 5, wherein said solvent is selected from the group consisting of methanol, dimethylformamide, methyl ethyl ketone, butyro lactone and acetone.

7. Improved apparatus for the recovery of acetylene from a feed gas stream containing acetylene and ethylene and produced by the cracking of hydrocarbon feedstock, which comprises: absorber column means for contacting said gas stream under pressure with an acetylene solvent in a quantity sufficient for the absorption of substantially all of the acetylene and some of the ethylene of said feed gas stream to form a loaded solvent solution heater means for warming and partially boiling said loaded solvent solution by passing through a first set of stream conduits of a recovery heat exchanger having a first set of non-interconnecting stream conduits passing therethrough, each set in heat exchange thermal contact with the others so as to form a temperature gradient across said recovery heat exchanger; trim heat kettle means for separating the resulting liquid/vapor mixture; means for passing the separated liquid phase to a second set of stream conduits of said recovery heat exchanger to cause the temperature thereof to drop substantially before said liquid phase passes on to a downstream further separation step for the removal of further purified acetylene product; and means for cooling warm denuded acetylene solvent to lower temperature initially by passage through a third set of stream conduits of said recovery heat exchanger means for further cooling before passage of said denuded acetylene solvent to said absorber column.

8. Improved apparatus for the recovery of acetylene from a feed gas stream containing acetylene and ethylene and produced by the cracking of hydrocarbon feedstock, which comprises: absorber column means for contacting said gas stream in a contacting zone under pressure with an acetylene solvent in a quantity sufficient for the absorption of all of the acetylene and some of the ethylene of said feed gas stream to form a loaded solvent solution; heater means for warming and partially boiling said loaded solvent solution by passing through a first set of stream conduits of a recovery heat exchanger having three sets of non-interconnecting stream conduits passing therethrough, each set in heat exchange thermal contact with the others so as to form a temperature gradient across said recovery heat exchanger; means for passing the resulting liquid/vapor mixture to a trim heater kettle wherein the vapor phase bypasses said heating zone and the liquid phase is further heated employing a heating medium external to the system to produce additional vapor which is recycled with said vapor phase to the liquid discharge region of said absorber column; means for passing said liquid phase to a second set of stream conduits of said recovery heat exchanger to cause the temperature thereof to drop substantially before said liquid phase passes on to a downstream further separation step for the removal of further purified acetylene product; and means for cooling warm denuded acetylene solvent to lower temperature initially by passage through a third set of stream conduits of said recovery heat exchanger means for further cooling before passage of said denuded acetylene solvent to said absorber column.

* * * * *